United States Patent [19]
Weber et al.

[11] Patent Number: 6,090,121
[45] Date of Patent: Jul. 18, 2000

[54] HIGHLY FLEXIBLE, REINFORCED SWAN NECK LIPOSUCTION CANNULAS

[76] Inventors: Paul J. Weber, 1 Seneca Rd., Ft. Lauderdale, Fla. 33308; Luiz B. DaSilva, 1995 Camino Ramon Pl., Danville, Calif. 94526; Michael R. Weber, 13906 Tern La., Clearwater, Fla. 33762

[21] Appl. No.: 09/474,305

[22] Filed: Dec. 29, 1999

Related U.S. Application Data

[63] Continuation-in-part of application No. 09/203,413, Dec. 2, 1998.
[51] Int. Cl.$^7$ ..................................................... A61B 17/32
[52] U.S. Cl. .......................................... 606/170; 606/167
[58] Field of Search ..................................... 606/170, 167, 606/184–185

[56] References Cited

U.S. PATENT DOCUMENTS

| | | | |
|---|---|---|---|
| 5,514,091 | 5/1996 | Yoon | 606/192 |
| 5,665,101 | 9/1997 | Becker et al. | 606/170 |
| 5,865,810 | 2/1999 | Perry et al. | 604/93 |

Primary Examiner—Michael Buiz
Assistant Examiner—Jonathan D. Goldberg
Attorney, Agent, or Firm—L. E. Carnahan

[57] ABSTRACT

The flexible cannulas are constructed of metal and plastic, with the metal cannulas having diameters of between 2.0 and 3.5 mm, and with the plastic cannulas having diameters greater than 3.5 mm (i.e., 3.5 to 6.0 mm). These long shaft flexible cannulas, when utilized in combination with a reinforced neck, allow the cannula point of entry to act as a fulcrum (with an optional interposed insert) in concert with the surgeon's guiding hand to deflect the cannulas. The cannula tip is preferably highly beveled with an adjacent set of three openings, and the cannula easily penetrates fibrous fat and may reach fat deposits relatively distant from the entrance wounds. The long shaft, highly flexible, reinforced swan neck cannulas move in an easily controllable manner within the subcutaneous tissue below the dermal envelope in an arciform fashion. Benefits include a reduced need to move a patient's body position intraoperatively. The swan neck has been reinforced to provide the needed additional stability at handle/shaft junction to help the surgeon increase leverage on the cannula shaft. The long, flexible plastic cannula shafts are provided central metal "memory" reinforcing wires of varying thicknesses along the length thereof which allow controlled rigidity of the long plastic shafts, and enable the cannulas to be bent into a semi-circle without breaking and yet return to their original shape.

20 Claims, 6 Drawing Sheets

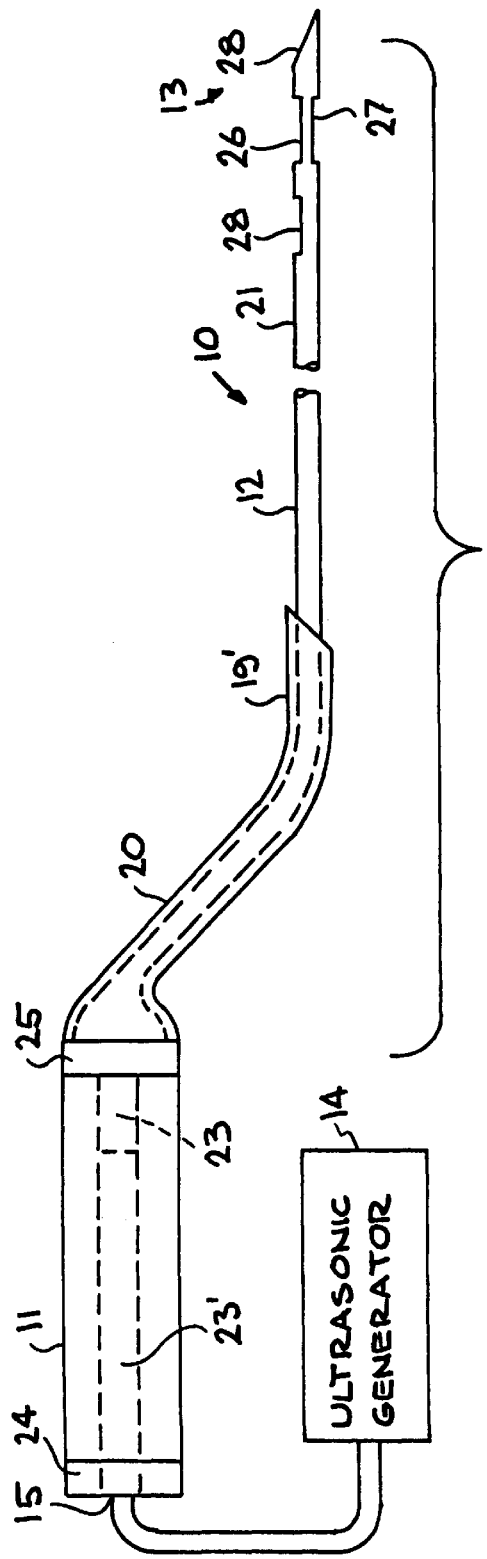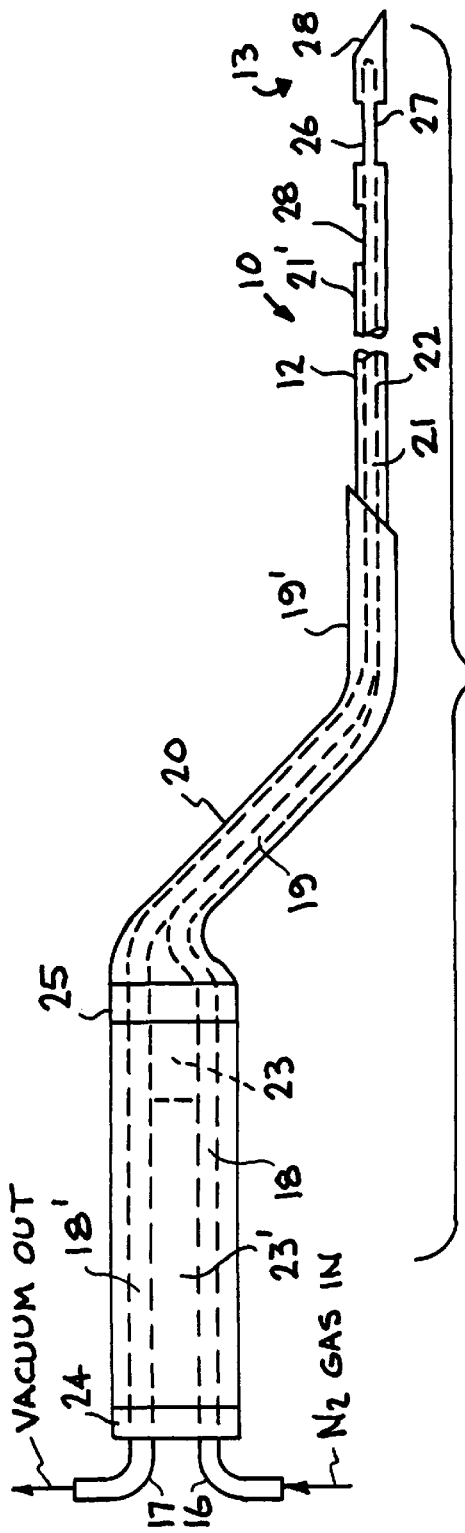

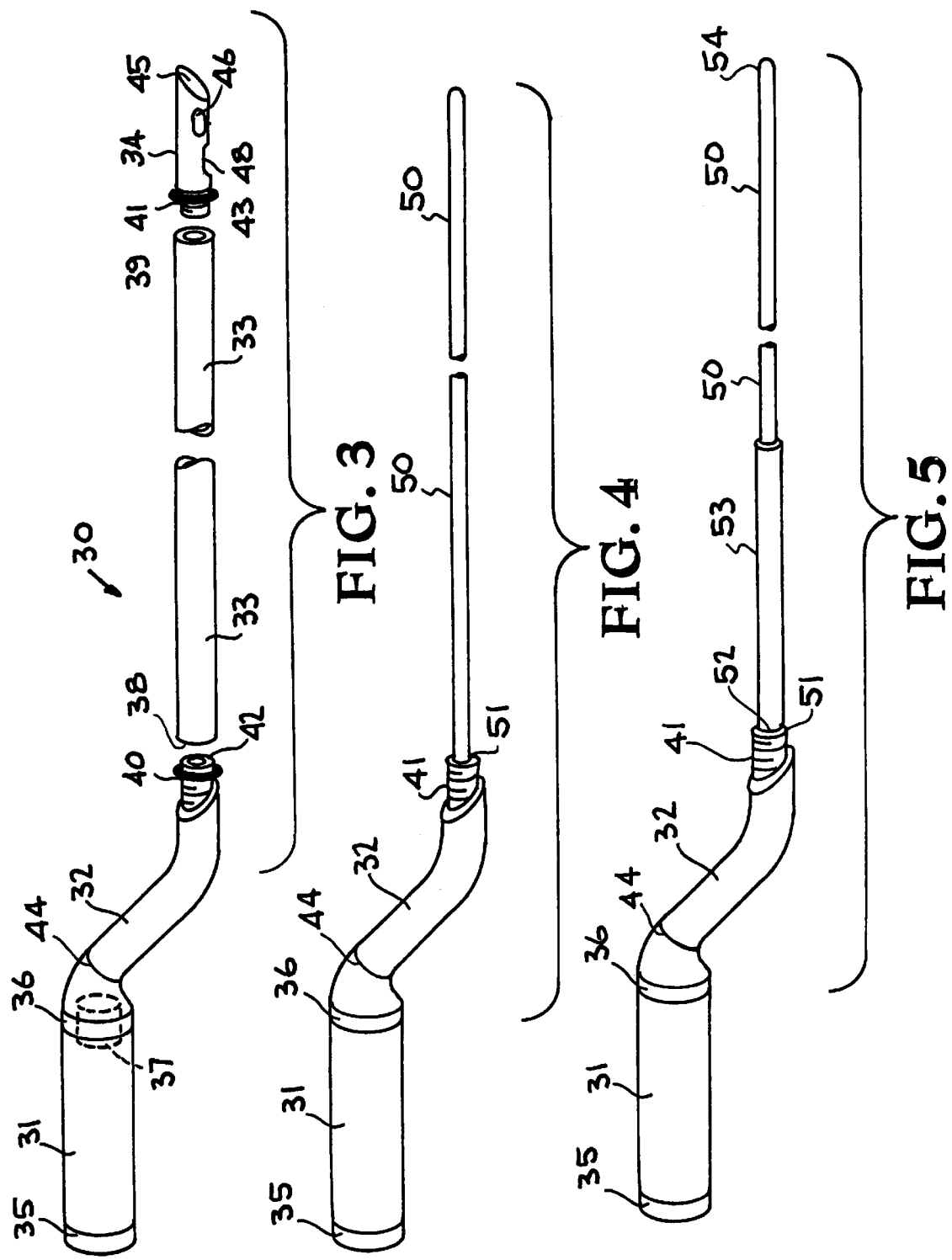

HIGHLY FLEXIBLE, REINFORCED SWAN NECK LIPOSUCTION CANNULAS

Background of the Invention

This application is a continuation-in-part of U.S. application Ser. No. 09/203,413 filed Dec. 2, 1998.

Background of the Invention

The present invention relates to liposuction apparatus, particularly to liposuction cannula shafts mounted via a swan neck to a handpiece, and more particularly to long, highly flexible metal or plastic cannula shafts which can be flexed to a semi-circular configuration and return to their original shape.

Liposuction, which literally means "fat suction", is a technique that pulls fat out of the body by means of teasing, pulling, scraping or suction. It can be used to reduce the volume of fat in many regions of the body, but is particularly effective in areas such as thighs and abdomen which contain genetically determined fat not responsive to diet or exercise. Liposuction is currently an established modality in cosmetic surgery, performed by surgeons as an elective operation, and is one of the most common procedures in medicine.

Traditional and ultrasonic liposuction cannulas usually are relatively rigid. The relative rigidity has its advantages and disadvantages. Advantages of relative rigidity include control, ease of manufacture and propagation of ultrasonic energy. Disadvantages of the rigidity include the fact that most areas of the human body are curviform and that the combination of straightness and rigidity places undesirable forces on the tissues adjacent to the cannula tips and tissues of the entrance wounds while the cannula is inserted in the patient. An article entitled "Reinforced Swan-Neck, Flexible Shaft, Beveled Liposuction Cannulas", P. J. Weber et al, The American Journal of Cosmetic Surgery, Vol. 16, No. 1, 1999, 41–47, described the use of a stainless steel shaft system with a reinforced swan neck for shaft diameters between 2.0 and 3.5 mm and drew comparisons with the prior art. Such a reinforced swan neck/shaft system is also described and claimed in above referenced copending Application Ser. No. 09/203,413 for use with sonic, ultrasonic and cooling systems. This system allows the cannula point of entry to act as a fulcrum (with an optional interposed insert) in concert with the surgeon's guiding hand to deflect cannulas with long flexible shafts and highly reinforced swan necks. The cannula tip is preferably highly beveled with an adjacent set of three openings. The system easily penetrates fibrous fat and may reach fat deposits relatively distant from the entrance wounds. The highly flexible, reinforced swan neck cannula shafts are intended to move in an easily controllable manner within the subcutaneous tissue below the dermal envelope in an arciform fashion. Benefits include a reduced need to move a patient's body position intraoperatively. A Teflon entrance wound insert (or anti-friction means), also described and claimed in copending Application Ser. No. 09/203,413, provides for reduced friction and tissue trauma at the dermal-epidermal level. The surgeon may require time to become proficient at maximizing the usage of novel cannula motions that occur as a result of using the cannula entrance point as a fulcrum and redirecting the distal shaft and tip of the cannula with an opposing hand. The novel motions arise from the minimally to highly arced possible cannula paths.

Many innovative cannula types and designs have been described and manufactured. Over time, the most commonly used variations have become the basis of traditional liposuction cannula design. Cannula designs may be categorized according to tip, aperture, shaft, handle, alloy and customization features. The cannula system described and claimed in copending Application Ser. No. 09/203,413 contains a unique combination of modifications and innovations not previously known. That 2.5–3.5 mm diameter metal shaft system was originally conceived to address the needs of ballerinas, fashion models, professional cheerleaders and the like's concerns about delicate fat removal with a minimum of cannula entrance wounds. Other issues that fostered a need for the cannula system included body curvature considerations and the need for intraoperative patient movement and positioning on the table. Previous attempts to address similar needs included the use of various long, rigid but slightly curved cannulas.

Many cannula tip designs are currently available. Each design has its positive and negative dynamics or attributes under varying conditions of usage. Liposuction cannula design dynamics have been summarized in the above referenced article by P. J. Weber et al. The tri-port bevel tip of copending Application Ser. No. 09/203,413 has been found to penetrate the fibrous fat with relative ease in combination with the systems herein described. Cannula passage in even the fibrous environment of previously suctioned patients appears facilitated. The tri-port bevel tip combination, although a very aggressive fat removing design, has yielded as little bleeding as we have seen with any other cannula tip design. Precise control over the aggressive action of multiple tip opening cannulas is recommended and may be gained by reducing the suction pump vacuum level to a suggested level of −12 Torr. The reinforced swan neck cannula should be moved slowly at first through the patient's tissues until the surgeon develops the necessary skills to consistently guide the cannulae to the appropriate target. Slow passage of these cannulae will usually provide aggressive liposuction and should be continuously monitored visually through the clear suction tubing and by target site palpation.

Swan neck modifications have been used in the past to aid the surgeon in directing the movement and placement of the cannula in close areas. Nonetheless, the forces customarily generated by the surgeon's arm during the course of surgery have been known to cause premature breakage in previous swan neck design junctions. Problems with earlier swan necks have included localized metal weakness, fracture, failure, undesired "bendability" and awkwardness. More positively, the reinforced swan neck of copending Application Ser. No. 09/203,413 provides a previously unattainable example that can now more fully demonstrate the many benefits of swan neck systems. Swan neck formations are especially helpful in combination with longer cannula shafts since traditional cannula linearity, length and rigidity may contribute to increase the probability that the surgeon's hand or cannula handle will bump or strike a patient's protuberance or convexity. Without swan neck modifications, the cumbersome length and rigidity of designs of previous cannulas caused surgeons to place additional stress on their own arms and the patient's tissues to guide the cannula shaft and handle in a workable fashion. In the above referenced 2.5–3.5 mm metal shaft cannula system, the swan necks have been specially and grossly reinforced. This reinforcement provides the needed additional stability at the handle/shaft junction to help a surgeon increase leverage on the cannula shaft and thus make use of the cannula entrance point as a fulcrum. Increased shaft leverage, in turn, allows the tip of the cannula to move in both traditionally expected and novel directions. To the surgeon who is not accustomed to using the new cannulas, this change and apparent unpredictability of tip movement may be alarming. Fortunately, with practice, tip motion can be perfected and the benefits of the new cannulas will become apparent.

Factors affecting a surgeon's selection of shaft length and character may be numerous. These factors may include the following: ease of tip location detection with shorter cannulas, concerns of increased handle/shaft junction breakage with increased length secondary to length-induced leverage, the secondary need for increased shaft diameter to increase strength (durability) when a longer cannula is desired, the advantage of minimizing the number of holes by using longer cannula. The reinforced swan neck allows for an increased range of workable cannula lengths for a variety of metal shaft diameters. These attributes, together with the special tip bevel, allow controllable tissue penetration with novel motions that should reduce the number of entrance incisions, hasten the procedure, reduce the need for patient repositioning. These benefits have been attained without apparent increased bleeding or complications. The use of high memory, extended length cannulas allows for movements and attributes heretofore considered problematic. For example, unique approaches to "hard-to-reach" areas, as well as decreasing the number of entry point openings, may modify a surgeon's repertoire.

Along with the tip modification and swan neck modification changes, shaft specification alterations have been made. The longer stainless steel shafts have been successfully used in all of our liposuctions performed numerous times. Stainless steel shafts in this cannula system are 2.0, 2.5, 3.0 and 3.5 mm in diameter. Currently available stainless steel tubing does not provide the flexibility or memory needed for proper function for shaft diameters exceeding 3.5 mm. However, certain alloys may enable an increase in diameter to about 5 mm.

Although shaft diameters between 2.0 and 3.5 mm provide surprisingly efficient and aggressive liposuction, many surgeons require cannula shaft diameters exceeding 4 mm to address obese patients and larger liposuction cases. However, metal cannulas with long shafts exceeding 3.5 mm in diameter of stainless steel were found on extensive testing to not possess the desirable qualities of a wide range of flexibility in combination with proper memory. The range for metal shafts is up to about 5.0 mm, preferably about 3.5 mm.

The present invention provides a new system using plastic cannula shafts with internal memory metal support wires which satisfies the need for cannula shafts having diameters of over 3.5 mm and up to 6–7 mm diameters. This plastic/support wire system has been tested successfully. The invention allows controlled rigidity of the plastic shafts and the cannulas can be bent into a semi-circle without breaking and yet still return to the original shape due to the internal metal support wire which provides the memory for the plastic shafts. The metal support wire decreases in thickness toward the distal end and may be covered with a Teflon coating to prevent excess load heating during autoclave sterilization of the plastic shaft. Also, the reinforced swan neck is provided with a disconnect which enables ready change of shafts of different diameters. Thus, the plastic cannula shaft system of the present invention, along with the above referenced metal cannula shaft system, provides a surgeon with the tools necessary to perform the complete spectrum of various liposuction procedures.

SUMMARY OF THE INVENTION

It is an object of the present invention to provide a long, highly flexible cannula shaft having a diameter range of about 2 mm to about 6 mm.

A further object of the invention is to provide a liposuction device which includes a reinforced swan neck and a plastic cannula shaft.

Another object of the invention is to provide a liposuction system with a plastic cannula shaft having an internal metal support wire.

Another object of the invention is to provide a plastic cannula shaft with a reinforcing memory wire whereby the shaft can be bent into a semi-circle and returned to its original shape.

Another object of the invention is to provide a swan neck with a coupling arrangement whereby a variety of diameter cannula shafts can be easily connected using a glued seal or O-ring/threads.

Another object of the invention is to provide a plastic cannula shaft with an internal memory wire that is less flexible at the proximal end than at the distal end of the shaft or which has uniform flexibility along its length.

Another object of the invention is to provide a plastic cannula shaft with an internal memory wire which is attached at the distal end and is free floating with the plastic shaft.

Another object of the invention is to provide an internal memory wire of a plastic cannula shaft with a thermal protective coating.

Other objects and advantages of the present invention will become apparent from the following description and accompanying drawings. The invention involves highly flexible, reinforced swan neck liposuctions cannulas, and particularly long, flexible cannula shafts that can be bent and return to their original shape. The invention is particularly directed to plastic cannula shafts that exceed 2.5 mm in diameter and which include a memory wire. While metal cannula shafts have sufficient flexibility up to a diameter of about 3.5–5.0 mm, plastic cannula shafts have sufficient flexibility in the 2.5–6.0 mm range to enable being bent in a semi-circle and return to the original shape when the plastic shafts include an internal memory wire. The internal memory wire is preferably constructed so as to be thicker in diameter at the proximal end of the cannula shaft. In addition, the memory wire may be coated with a heat resistive material while the plastic cannula shaft is steam autoclaved or is utilized with an ultrasonic energy arrangement. Also, the memory wire may be attached at the distal end of the cannula shaft and be free floating adjacent the proximal end of the shaft.

BRIEF DESCRIPTION OF THE DRAWINGS

The accompanying drawings, which are incorporated into and form a part of the disclosure, illustrate embodiments of the invention and, together with the description, serve to explain the principles of the invention.

FIG. 1 is a side view of an embodiment of a liposuction device including a handle removably connected to a hollow, flexible cannula shaft having a high memory of recovery, integrated with a reinforced swan neck and including a triport tip having a bezel, and with the handle connected to an ultrasonic generator.

FIG. 2 illustrates the device of FIG. 1 constructed to be connected to a pressure equalizer and to a vacuum, with the fluid passageways shown in dash lines.

FIG. 3 is a longitudinal partially exploded view of an embodiment of a liposuction device utilizing a separate swan neck and a removable shaft tip.

FIG. 4 illustrates an embodiment of a metal memory wire to be used in a hollow cannula shaft of high flexibility and low memory.

FIG. 5 illustrates the embodiment of FIG. 4 with the metal shaft having an increased thickness at the proximal end, and may be of a thin solid material or a thick hollow material.

DETAILED DESCRIPTION OF THE INVENTION

Figure 6:
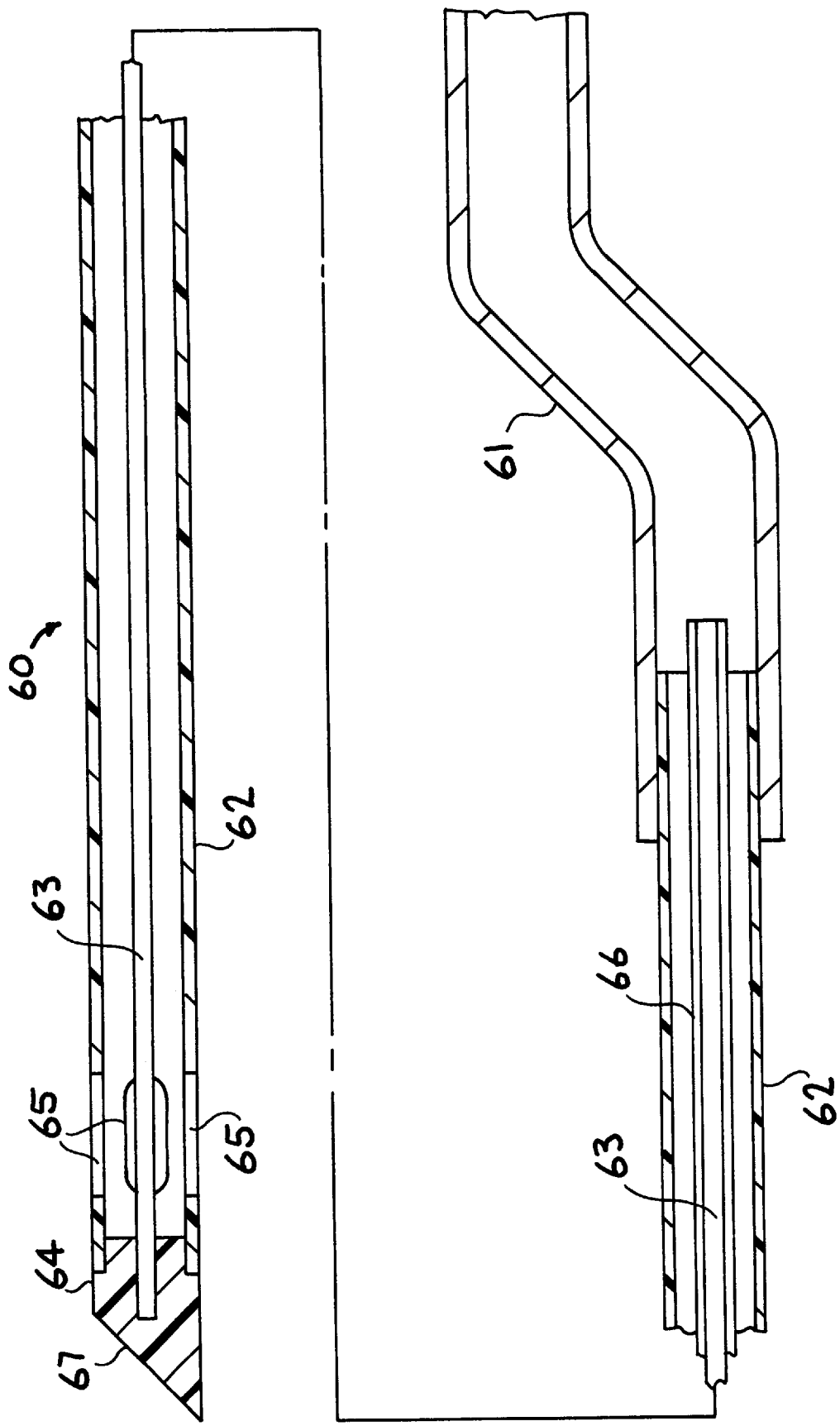
FIG. 6 illustrates an embodiment of a plastic cannula shaft integral with the swan neck and including a free floating memory wire secured to the shaft at the distal end.

The present invention is directed to highly flexible, reinforced, swan neck liposuction cannulas that, depending on the diameter of the cannula shaft, can be constructed of a metal or a plastic. Long metal cannula shafts having a diameter of up to about 3.5 mm have some flexibility and can be effectively utilized for various liposuction procedures, but metal cannula shafts above a diameter of about 3.5 mm have insufficient non-breaking flexibility and thus long plastic cannula shafts made in accordance with the present invention having an internal memory wire and having diameters of up to about 6 mm can be effectively utilized.

This plastic/memory wire system allows controlled rigidity of the plastic shafts; the cannulas can be bent into a semi-circle without breaking and yet still return to the original shape. Importantly, the plastic shafts must withstand repeated autoclaving without being deformed or losing their desirable properties. Additionally, the shafts needed to be internally reinforced as extensive testing in vivo without reinforcement demonstrated a need for a graded strength along the shaft in more fibrous liposuction patients and locations. The reinforcing "memory" wires are specially made to be slightly less flexible in the proximal portions of the shaft and more flexible toward the distal tip, thus allowing a convenient gradation of shaft flexibility. A reinforced swan neck disconnect system is used with any number of different plastic shaft diameters, significantly lowering the cost per unit. The wide range of modified plastic shaft performance makes it possible to predictably suction the mid-lower back from an incision in the umbilicus without rotating the patient, as was previously necessary.

Predictable flexibility and excellent memory are imperatives for the metal and plastic shafts. In this system, it is not preferred that the surgeon should be able to bend a cannula prior to placement into the patient and have the cannula maintain the bent shape. Surgeons that desire this quality may find it available in preexisting systems that eventually weaken and require replacement of the cannulas secondary to stress fractures. Also, routine bending by hand is not smooth, regular or uniform, but bumpy.

The benefits of increased flexibility and "memory" can be demonstrated in at least two noteworthy behaviors of the new cannula system. The first, called "opposing motion", occurs if less than one-half of the cannula shaft length has been introduced into the patient, then forcing or pointing the cannula handle to the right will move the cannula tip to the left in the patient and visa versa. Lifting the handle will usually direct the tip downward deeper into the patient's subcutaneous tissue. Second, the cannula tip and distal shaft can be made to ricochet (in conjunction with the 5 aforementioned "opposing motion action" exerted by the cannula handle) within subcutaneous fat of the patient.

Most liposuction texts and authorities continue to advocate the spokewheel technique of cannula passage. The spokewheel technique, in essence, may be considered as a series of 90 degree (or any number of degrees) intersecting lines. Another potential benefit of the cannula system of this invention is that by using the principle of "opposing motion action" a surgeon can approximate desirable criss-cross tunneling via increasingly distant entrance wounds.

An apparent benefit of the use of the long, flexible, reinforced swan neck system is the ability to perform liposuction a relatively great distance from the cannula entrance wounds. In patients with a hereditary predisposition to pigment at entrance wounds, this benefit may be significant. Undesirable pink marks can be reduced in fashion models. Typical cannula entrance wound-suction site pairs include the following: posterior flank suctioned from anterolateral abdominal entrance wounds, knees suctioned from superiormost thigh wounds, inner crural thighs suctioned from medial knee wounds, and ankles suctioned from knee wounds. The use of metal 2.5–3.5 diameter cannula appear most helpful in approaching the excess fibrofatty material in the infragluteal area from a medial knee incision in patients who are not over 25% in excess of ideal body weight. For patients who are in excess of this ideal weight parameter, the plastic shaft with reinforcing wire are of benefit. The relatively vertical criss-crossing effect has allowed for ridge free protuberance reduction with no notable buttock ptosis.

There may be disadvantages to the long flexible cannula system. The use of fewer holes to approach more sites will, by necessity, increase the duration of friction and leverage pressure applied to each entrance wound. Longer cannulas, dry operating room air and proteinaceous material accumulation on the outside of the cannulas can also increase entrance wound friction. The friction may be further increased if a surgeon attempts to use the entrance wound as a fulcrum or use the "opposing motion action" technique. Although all entrance wounds will naturally scar, those that are traumatized the most will remain pigmented the longest, especially in pigment prone patients.

Figure 11:
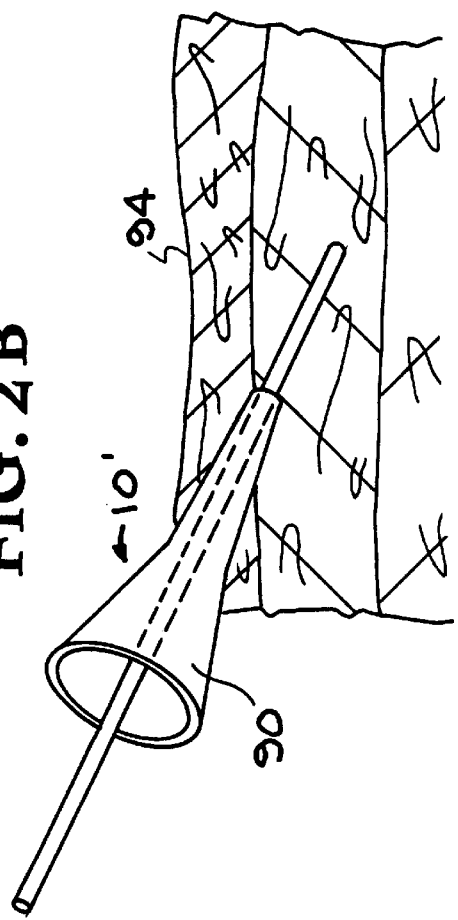
FIGS. 10–11 illustrate an embodiment of an anti-friction insert adapted for insertion into an incision as shown in FIG. 11.
Figure 10:
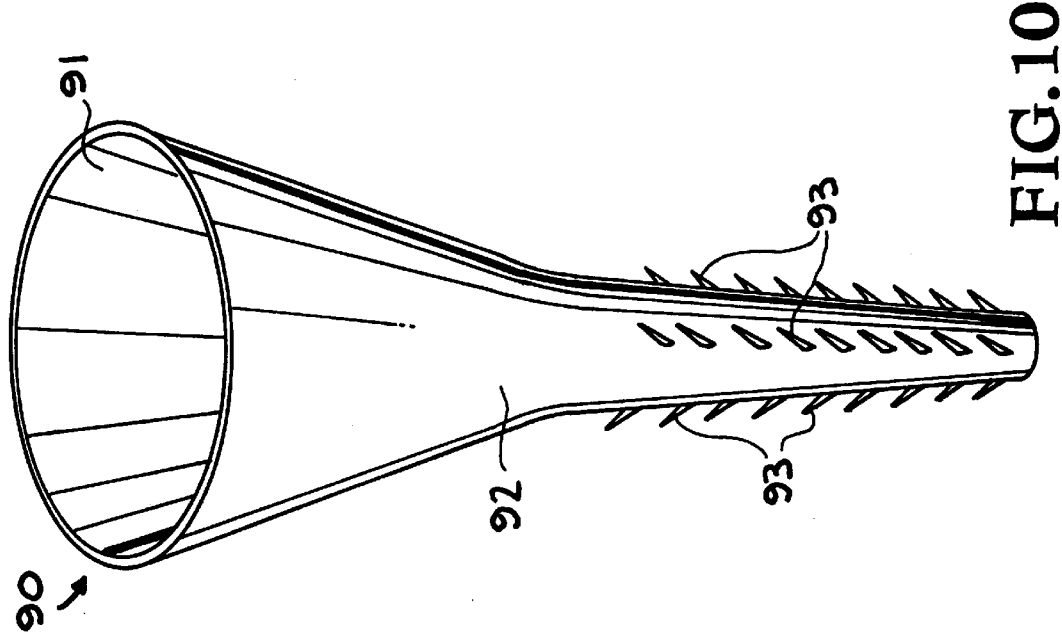

Aside from coating the external portion of cannula shafts with non-stick polymers (that eventually wear off) and applying lubricating jellies to the entrance wounds, another solution to the entrance wound friction problem is the use of temporary intraoperative plastic stents or anti-friction means (such as shown in FIGS. 10–11). Unfortunately, previously available screw-in devices are of thicker materials and damage skin entrance wounds via pressure more than the anti-friction means hereinafter. The preferred anti-friction means is a conical Teflon. The insert is of low friction inside (to aid in cannula passage) and higher friction outside (to reduce the tendency to extrude on cannula backstroke) and can be easily and quickly applied to or removed from any size liposuction entrance wound. Outside friction is increased predictably as a result of projections, unidirectional notches or slits in the insertional exterior portion of the anti-friction means. The non-insertional portion of the anti-friction means may have a single row of oppositely directed notches or slits to prevent over insertion of the device.

Figure 2A:
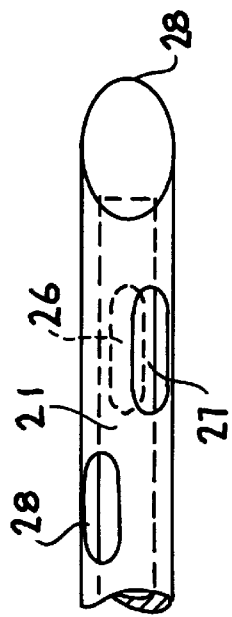
FIG. 2A is a partial top view of an embodiment of the multiport tip of FIGS. 1 and 2.
Figure 2B:
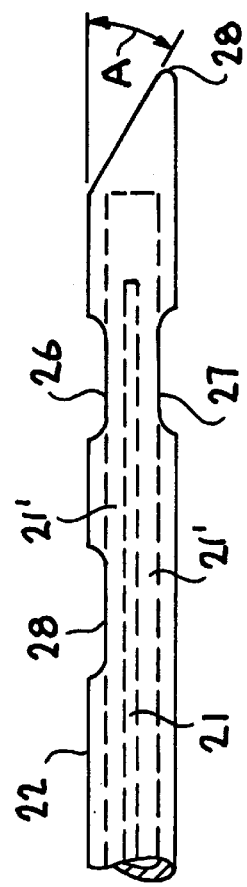
FIG. 2B is a partial side view of the multiport tip of FIG. 2A illustrating the fluid passageways in dashed lines.

Referring now to the drawings, FIGS. 1, 2, 2A and 2B illustrate an embodiment of a liposuction device (generally indicated at 10) which includes a handle or handpiece (generally indicated at 11) and an integral reinforced swan neck/cannula shaft (generally indicated at 12) with the cannula shaft having a tip section (generally indicated at 13). As shown in FIGS. 1 and 2, the handpiece 11 is connected to an ultrasonic generator 14 via a coupling 15, to a fluid supply (such as N2 gas) via a connection tube 16, and a vacuum source via a connection tube 17. As shown in dash lines in FIGS. 2 and 2B, the handpiece 11 includes a channel or tube 18 connected to a channel or tube 19 in reinforced swan neck section 20 and channel or tube 21 in cannula shaft section 22 of the reinforced swan neck/cannula shaft for directing fluid material through the handpiece to the tip section 13, which is suctioned out via a channel or tube 19' and a channel or tube 18'. The fluid cooling, aspiration and ultrasonic arrangements for the device 10 are known in the art and further detail is deemed unnecessary. The handpiece 11 also contains a microprocessor 23 located in a channel 23' (shown by dash lines) for controlling fluid passage through the device 10.

The handpiece 11 also includes removable (threaded) end sections 24 and 25 which are connected to the coupling 15 and connection tubes 16 and 17 and to the reinforced swan neck section 20, the shaft section 22 being fixedly secured in or integrally formed with the reinforced swan neck section 20. The fluid connection 16 is connected to a tube 18 (indicated by dash lines) which extend via a connection to tube 19 in the reinforced swan neck section 20 to the tip section 13 (as seen in FIG. 2B) whereby cooling or cleaning fluids may be introduced at the tip section 13. If desired, the handpiece 11 and swan neck section 20 may be connected by commercially available quick connect assemblies.

Tip section 13 of cannula shaft 22 is of a triport type with a beveled end or bezel. As seen more clearly in FIGS. 2A and 2B, the tip section includes a pair of openings 26 and 27 and a third opening 28 spaced from openings 26 and 27, and a tapered or beveled end or bezel 29 having an angle (,A,) of inclination of about 20 to 60 degrees, preferably about 35 degrees.

The swan neck section 20 is reinforced for several reasons. Reinforcement provides the needed stability to help a surgeon increase leverage on the cannula shaft section 22 and to use it as a guide in combination with the wound opening. The reinforcement may consist of a flexible thickening material (such as thermoplastic or thermoset polymers) or a wire reinforcement or a metallic sleeve or jacket cannula. Preferably, the reinforcement comprises a thickening. The shaft is constructed of a material having excellent flexibility and memory characteristics. Metals and plastics are suitable materials of construction. Examples of plastic material include olefin polymers, fluorocarbon polymers and synthetic rubbers. Preferably polypropylene, polyethylene and tetrafluoroethylene, and more preferably high density polyethylene, are utilized. Examples of suitable metals include aluminum, cold rolled steel, stainless steel, titanium or a titanium alloy.

As pointed out above, the cannula shaft section 22 is constructed of metal (such as stainless steel or non-oxidizing alloys) with a diameter of about 2.0–3.5 mm and up to about 5.0 mm. The shaft section 22 is sufficiently rigid to permit repeated and controlled advancing strokes through the tissue but is sufficiently flexible to enable an amount of bending. The reinforced swan neck section 20 allows for longer insertional lengths of the shaft section 22 (which range from about 15 cm to about 35 cm, and preferably from 25–33 cm). The excised tissue from the surgical site is aspirated via channels 21', 19' and 18' to a vacuum line 17 and to a collection means (not shown). Irrigating fluid (such as saline, antiseptic, anesthetic solutions, hyaluronidase, heparin and epinephrine) or cooling fluid such as an inert gas (nitrogen, for example) are directed through tube 16 and channels 18, 19 and 21 to tip section 13, and are aspirated out with the removed fatty tissue FIG. 3 illustrates an embodiment of a liposuction device wherein the cannula shaft is removably connected to the swan neck, the swan neck is removably connected to the handpiece, and the tip is removably connected to the cannula shaft. As shown, the device (generally indicated at 30) basically includes a handpiece 31, a swan neck 32, a cannula shaft 33 and a triport beveled tip 34. Handpiece 31 includes removable end 35 and 36, with a microprocessor 37 mounted in end 36. Shaft 33 is provided at each end 38 and 39 with internal threads that cooperate with threaded end 40 of swan neck 32 and threaded end 41 of tip 34. A pair of O-ring seals 42 and 43 are located about threaded ends 40 and 41. While not shown, swan neck 32 is threadedly connected at 44 to removable end 36 of handpiece 31 in a similar manner. Tip 34 includes a beveled end 45 and three openings (as in FIGS. 2A–2B) with only two openings shown (46 and 48). The cannula shaft 33 and tip 34 is preferably made of metal if the diameter is less than about 3.5 mm, or made of plastic if the diameter is greater than about 3.5 mm.

If the cannula shaft of FIG. 3 is constructed of plastic with a diameter greater than about 3.5 mm, a flexible metal guide shaft or memory wire (as shown in FIG. 4) is located internally to provide memory for the plastic shaft (to return it to its original shape after bending). Components of FIG. 4 corresponding to FIG. 3 are given corresponding reference numerals. As seen in FIG. 4, a memory wire or guide shaft 50 is secured in an opening 51 of the threaded end 40 of swan neck 32, with wire 50 being of a smaller diameter than the inner diameter opening 51 of end 40 to allow passage of fluids and/or aspiration of fatty tissue to pass therebetween, or the memory wire 50 may be made hollow to provide an aspiration path.

To enable the plastic cannula shaft to bend up to a semi-circle and return to its original position, it is preferred that the memory wire or guide shaft of FIG. 4 have a thicker proximal end than distal end. FIG. 5 illustrates an embodiment wherein the proximal end 52 of the wire 50 of FIG. 4 is provided with a metallic coating 53. If desired, the wire 50 may be tapered or contain tapered sections which decrease from the proximal end 52 to the distal end 54.

Figure 7:
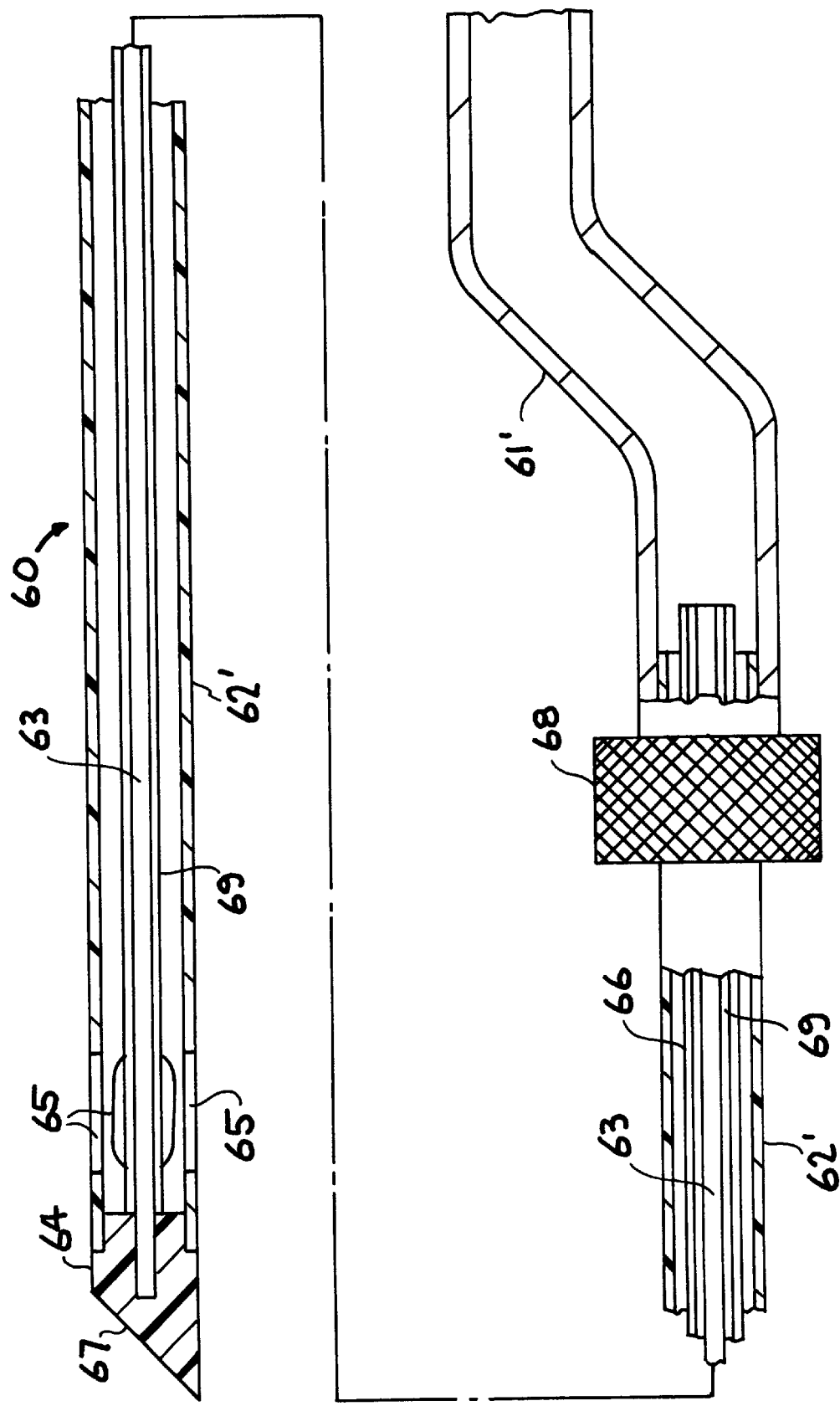
FIG. 7 illustrates an embodiment similar to FIG. 6 but with the plastic cannula shaft removably attached to the swan neck and with a heat protective coating on the memory wire.

FIG. 6 and 7 illustrate embodiments of a free floating memory wire for a plastic cannula tube having a diameter of greater than about 3.5 mm, with FIG. 7 illustrating a thermal (heat resistant) coating on the memory wire.

As shown in FIG. 6, a swan neck/cannula shaft generally indicated at 60 comprises a swan neck 61 and a plastic cannula shaft 62 which is secured to or integral with swan neck 61. A free floating metal memory wire 63 is mounted within cannula shaft 62 via a plug 64 located near the distal end of shaft 62, which is provided with one or a plurality of openings 65, and plug 64 includes a beveled end 67 (as in FIGS. 2A–2B). The memory wire 63 is provided with an increased thickness or layer 66 at the proximal end of shaft 62. The memory wire 63 extends into the swan neck 61 but terminates short of the fist bend therein (as shown). By way of example, the plastic cannula shaft 62 has a diameter of from about 3.5 mm to about 6.0 mm, with the memory wire 63 being constructed of stainless steel with a diameter of 1 mm to 6 mm and the layer 66 may be composed of stainless steel with a diameter of 1.5 mm to 6.5 mm, with plug 64 composed of PEEK (polyarylether ketone polymer) made by Victrex, Westchester, Pa., plastic Delrin, epoxy or glue. The memory wire 63 and layer 66 may be integrally fabricated, if desired. Shaft 62 may terminate in a beveled or bezel tip 67 which may be constructed as shown in FIGS. 1–2B or FIG. 3.

FIG. 7 illustrates a liposuction device similar to FIG. 6 except for the connection of the cannula shaft to the swan neck and the addition of a thermal protective layer for the memory wire.

Corresponding components have been given corresponding reference numerals. As shown, the swan neck 61' of device 60' is connected to cannula shaft 62 by removable coupling 68, and a layer 69 of thermal insulation material (such as Teflon or hydrocarbon based polymers) is coated on the memory wire 63 and thickening layer 66 so as to prevent excessive heating of the memory wire 63 when steam autoclave sterilization or ultrasonic energy is applied to the cannula shaft.

Figure 8:
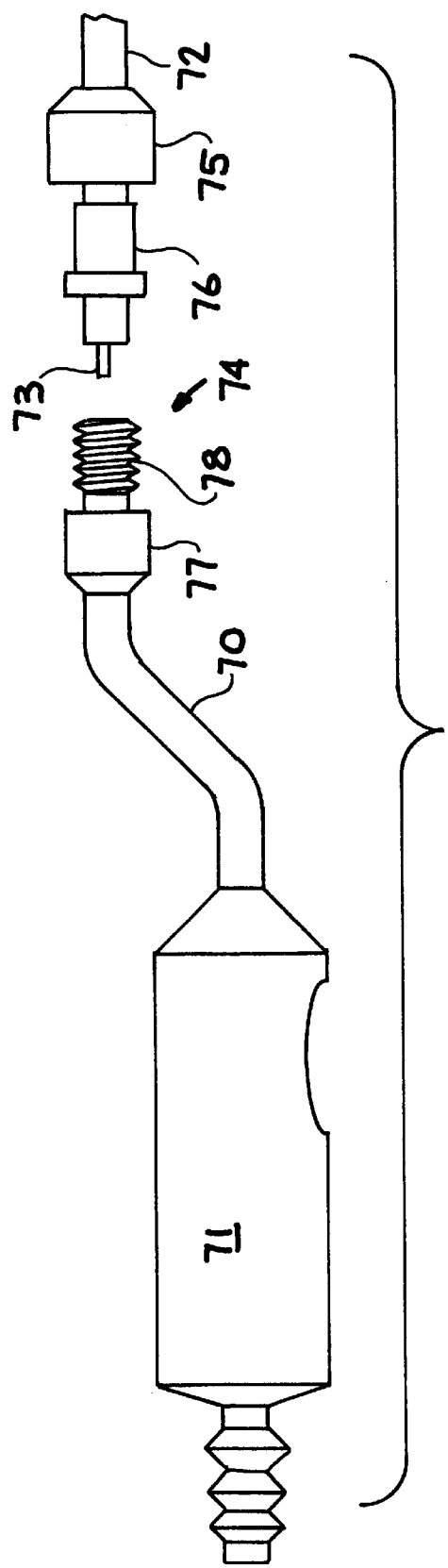
FIG. 8 illustrates a liposuction device wherein the swan neck and plastic cannula shaft with memory wire are connected by a threaded coupling to enable rapid interchange of different diameter cannula shafts using the O-ring/threaded connection.

FIG. 8 illustrates a liposuction device having a coupling mechanism to enable quick interchange of different size (length or diameter) cannula shafts. As shown, a swan neck 70 is mounted to a handpiece 71 (as shown in either FIGS. 1–2B or FIG. 3) and the swan neck 70 is removably connected to a cannula shaft 72 having therein a guide or memory wire 73 (as shown in FIGS. 4–5 or 6–7) by a coupling mechanism (generally indicated at 74). Coupling mechanism 74 includes an internally threaded member 75 and compression seal 76 located on cannula shaft 72, and a member 77 having a threaded end 78 secured to swan neck 70 whereby cannula shaft 72 and memory wire 73 are inserted into member 77, and member 75 is threaded onto the thread end 78 of member 77 such that the compression seal 76 is deformed and retains the cannula shaft 72 within member 77. Simple removal of the thread member 75 from threaded end 76 enables quick removal of the shaft 72 whereby a different shaft having a threaded member 75 and compression seal 76 can be attached to the swan neck 70.

Figure 9:
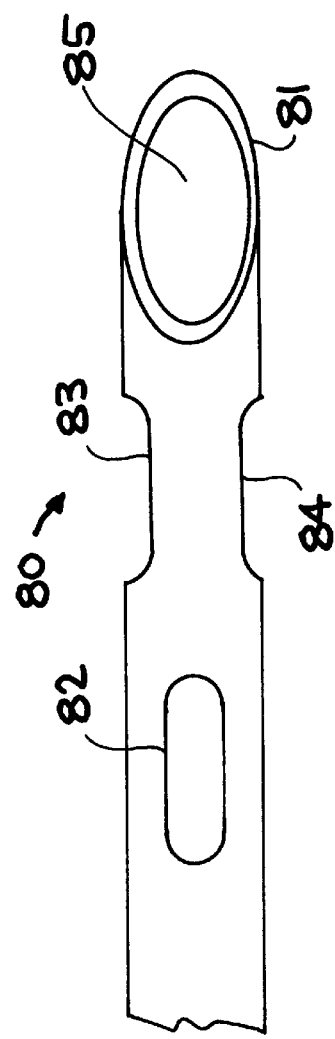
FIG. 9 illustrates another embodiment of the multiport tip similar to FIGS. 2A and 2B but with one opening located intermediate of and spaced from the other two openings. Hole orientation is not critical.

FIG. 9 illustrates an embodiment of a triport tip similar to FIGS. 2A–2B. As shown, the tip (generally indicated at 80) is provided with a beveled end 81 (as in FIGS. 2A–2B) and with three openings 82, 83 and 84. Opening 82 is located in longitudinal spaced relation to openings 83 and 84 (as in FIGS. 2A–2B) but has an axis which extends an equal distance between opening 83 and 84, which differs from the location of opening 28 relative to openings 26 and 27 of FIGS. 2A–2B. The beveled or bezel end 81 is provided with a plug 85 (as in FIGS. 6 and 7). The tip 80 of FIG. 9 may be integral with the cannula shaft (as in FIGS. 2A–2B) and removably connected to the shaft (as in FIG. 3).

FIG. 10 illustrates an embodiment of an anti-friction insert adapted to be inserted into an incision (as shown in FIG. 11). The insert (generally indicated at 90) comprises a funnel shaped member 91 having a lower section 92 provided with a plurality of protruding members 93 which extend at an angle with respect to section 92 which (as shown in FIG. 11) function to prevent the insert 90 from being pulled from an incision in an area of fatty tissue 94 when a liposuction device 10' (such as shown in FIGS. 1–2B, 3 and 6–7) is maneuvered to remove fatty tissue or is withdrawn from insert 90.

It has thus been shown that the present invention provides a liposuction device that can be effectively utilized with various diameter cannula shafts, and wherein plastic cannula shafts with memory or guide wires are effectively utilized wherein shaft diameters of greater than about 2.5 mm are desired. The plastic shaft with metal memory wires can be bent into a semi-circle and returned to its original shape thereby enabling extensive use of the liposuction device without requiring patient movement. Thus with the use of metal cannula shafts of diameters under about 3.5–5.0 mm attached to a reinforced swan neck and plastic cannula shafts with memory wires of diameters greater than about 2.5 mm attached to a reinforced swan neck, the surgeon is provided with tools that enable extensive liposuction applications.

While particular embodiments, materials, parameters, etc. have been described and/or illustrated to exemplify and teach the principles of the invention, such are not intended to be limiting. Modifications and changes may become apparent to those skilled in the art, and it is intended that the invention be limited only by the scope of the appended claims.

What is claimed is:

1. In a liposuction device, the improvement comprising:
   a reinforced swan neck, and
   a cannula shaft mounted to said reinforced swan neck and constructed of material selected from the group consisting of metal and plastic having a memory wire located therein.

2. The improvement of claim 1, wherein said cannula shaft has a diameter of less than about 5.0 mm and is constructed of a metal.

3. The improvement of claim 1, wherein said cannula shaft has a diameter of greater than about 2.5 mm and is constructed of a plastic having a memory wire therein.

4. The improvement of claim 3, wherein said memory wire has different sized cross-sections with a larger cross-section located adjacent a proximal end of said cannula shaft.

5. The improvement of claim 4, wherein said larger cross-section of said memory wire is free floating.

6. The improvement of claim 5, wherein said larger cross-section of said memory wire has a terminal end extending into said reinforced swan neck.

7. The improvement of claim 3, wherein said memory wire is secured at one end within said reinforced swan neck.

8. The improvement of claim 3, wherein said memory wire is secured at one end in a distal end of said cannula shaft.

9. The improvement of claim 8, wherein said one end of said memory wire is secured in a plug located within said distal end of said cannula shaft.

10. The improvement of claim 3, wherein said memory wire is provided with a thermal coating.

11. The improvement of claim 3, wherein said memory wire has a greater cross-section at a proximal end of said cannula shaft than at a distal end of said cannula shaft.

12. The improvement of claim 1, wherein said reinforced swan neck and said cannula shaft are fixedly secured together.

13. The improvement of claim 1, wherein said cannula shaft is removably connected to said reinforced swan neck.

14. The improvement of claim 1, wherein said cannula shaft includes a multiport tip section.

15. The improvement of claim 14, wherein said multiport tip section is removably connected to said cannula shaft.

16. The improvement of claim 14, wherein said multiport tip section includes a beveled end extending at an angle of about 30 degrees to about 60 degrees.

17. The improvement of claim 1, wherein said cannula shaft is provided with a tip section having a plurality of spaced openings.

18. The improvement of claim 17, wherein said plurality of spaced openings includes one opening longitudinally spaced from at least one other opening.

19. A liposuction device, including:

a handpiece, a reinforced swan neck operatively mounted to said handpiece, and a flexible cannula shaft operatively connected to said reinforced swan neck, said flexible cannula shaft being constructed of a material having a diameter less than about 5.0 mm or constructed of a different material having a diameter of greater than about 2.5 mm and having a tip section with a plurality of openings, wherein said flexible cannula shaft is provided with a memory wire operative mounted within said flexible cannula shaft.

20. The liposuction device of claim 19, wherein said different material is composed of plastic or silicone polymer.

\* \* \* \* \*